United States Patent [19]

Hayashi

[11] 4,130,007

[45] Dec. 19, 1978

[54] FOOTWEAR TESTER

[75] Inventor: Hideki Hayashi, Kurume, Japan

[73] Assignee: Nippon Rubber Co., Ltd., Tokyo, Japan

[21] Appl. No.: 853,891

[22] Filed: Nov. 22, 1977

[30] Foreign Application Priority Data

Nov. 25, 1976 [JP] Japan .................. 51-140722

[51] Int. Cl.² ............................ G01N 3/56
[52] U.S. Cl. ........................ 73/7; 73/812; 73/172
[58] Field of Search ............. 73/7, 172, 91, 100, 73/432 SD; 35/57

[56] References Cited

U.S. PATENT DOCUMENTS

| | | | |
|---|---|---|---|
| 1,906,175 | 4/1933 | Millet | 73/7 |
| 2,013,643 | 9/1935 | Bliss | 73/100 |
| 2,025,790 | 12/1935 | Thompson | 73/7 |
| 2,048,837 | 7/1936 | Byers | 73/100 |
| 2,638,776 | 5/1953 | Aines | 73/7 |
| 3,427,859 | 2/1969 | Taub | 73/7 |
| 3,516,281 | 6/1970 | Taub | 73/7 |
| 3,608,372 | 9/1971 | Hovey | 73/100 |

FOREIGN PATENT DOCUMENTS 164455  8/1963  U.S.S.R. ............. 73/100

*Primary Examiner*—S. Clement Swisher
*Assistant Examiner*—Denis E. Corr

[57] ABSTRACT

Footwear tester comprising a machine stand, a prime mover mechanism mounted on the machine stand, a footwear block supporting mechanism which supports freely a footwear block to be automatically advanced and retreated by said prime mover, a footwear block inclining mechanism which performs changes of the posture of said mechanism for supporting freely the footwear block, front operation mechanism and rear operation mechanism for controlling changes of the posture of said footwear block from the outside, and lift mechanism for bringing up and down a ground stand, wherein said respective mechanisms are interconnected with one another so as to control changes of the posture of the footwear block.

10 Claims, 16 Drawing Figures

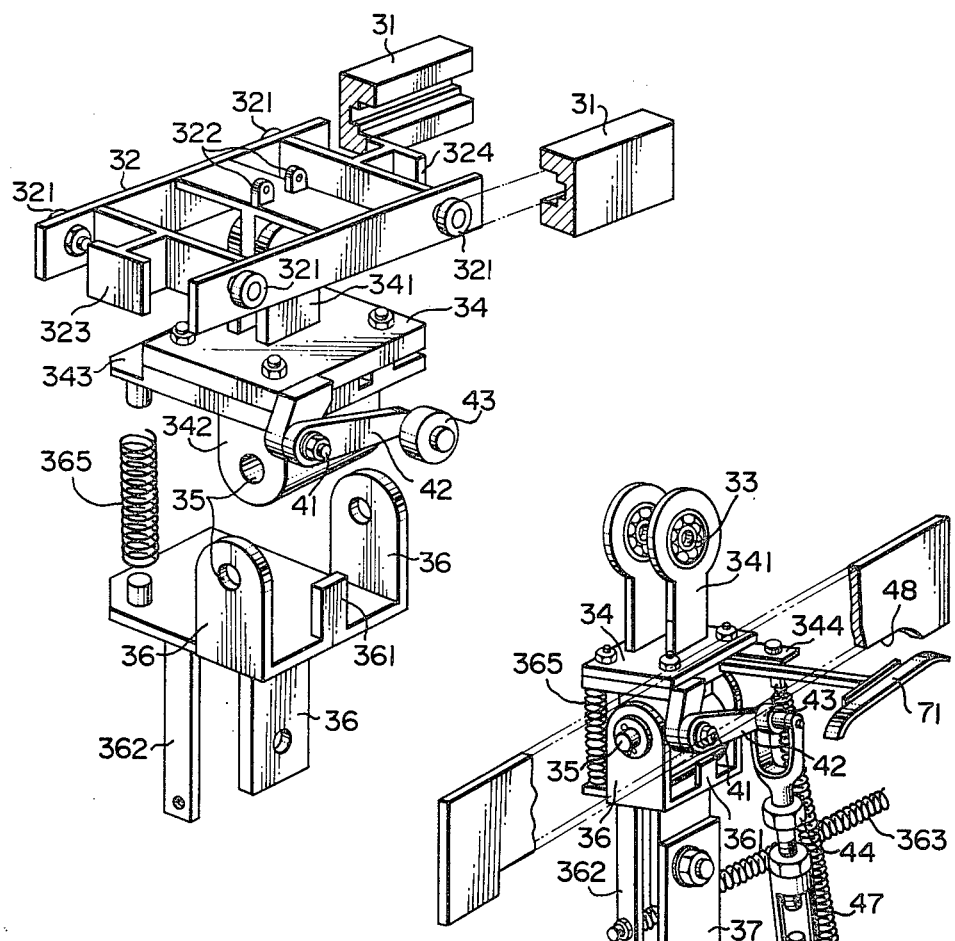
FIG. 2
FIG. 5
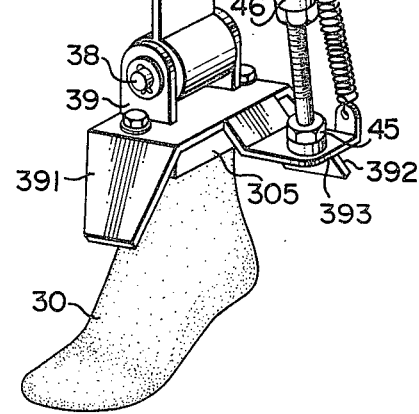

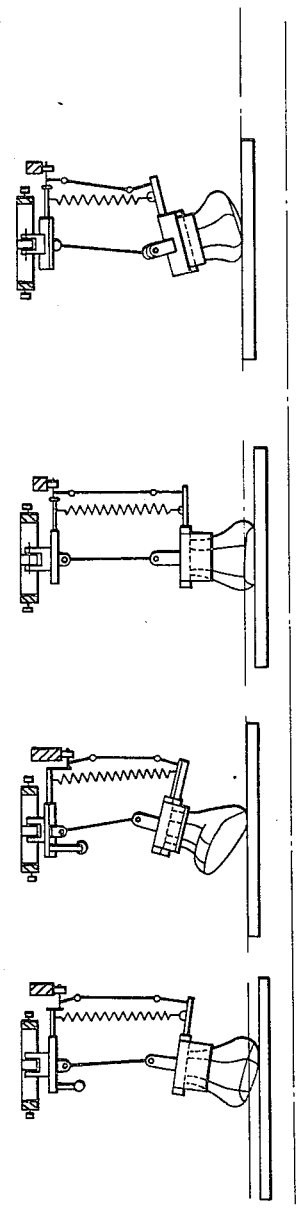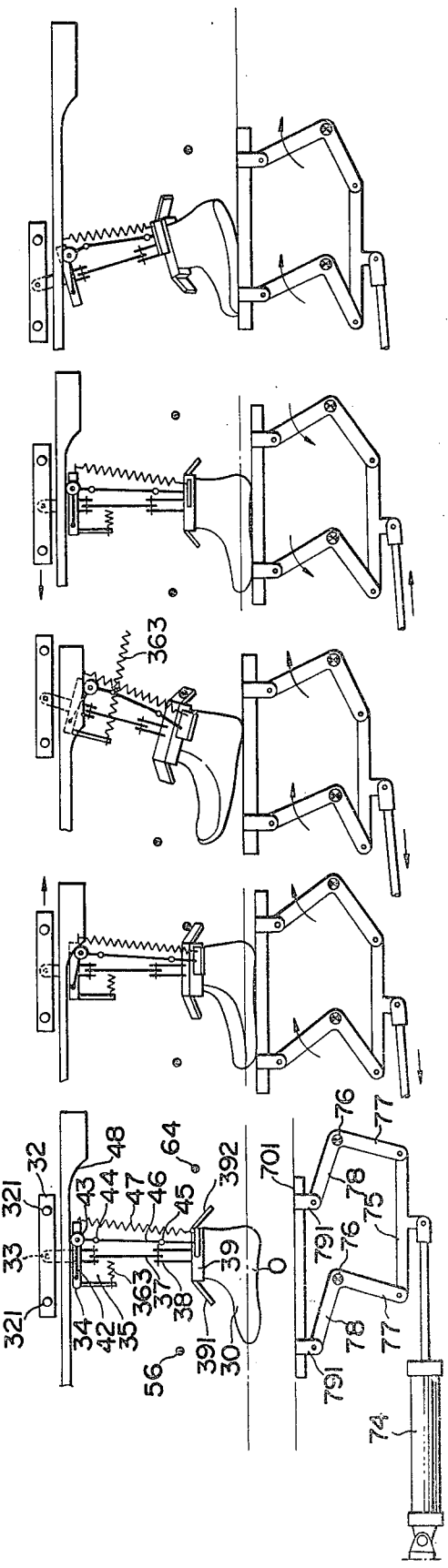

FOOTWEAR TESTER

The present invention relates to a structure of a footwear tester by which a test of footwears corresponding to the practical wearing test can be mechanically performed.

The durability of footwear is influenced by various factors such as breakdown of the outer instep portion owing to abrasion of the sole. In order for a footwear to have a good durability, it is necessary that the strength must be balanced in respective parts. Various footwear testers have heretofore been proposed, but these testers are designed so that footwear are subjected to simple frictional movements and in many cases, test results are not coincident with results obtained when the footwear are actually worn. Accordingly, importance is attached on the so-called practical wearing test in which a footwear is actually worn by a man and the strength of the respective parts is checked. In this test, however, since the wearing test time is inevitably limited, it is impossible to obtain test results in a short time.

According to the footwear tester of the present invention, the operation state of a footwear block to which a footwear to be tested is attached is made as approximate as possible to the practical movement state of a foot and it is possible to obtain test results quite similar to results of the practical wearing test, especially the practical wearing test conducted under specific conditions. More specifically, as a result of of investigations of movements of the foot and leg, it was found that when a footwear block is connected to a freely supporting mechanism corresponding to the leg, contrary to the practical movement of the leg this freely supporting mechanism is inclined back and forth and in the lateral direction while setting and fixing the position of the footwear block, actions corresponding to the respective postures of the foot are given to the footwear block by another accompanying mechanism and when a ground stand is brought up and down according to the postures of the foot, actions corresponding to the movements of the leg and foot can relatively be given to the footwear block which is fixed at one set position. Based on this finding, we have now completed the present invention.

When the movement of the foot during walking is carefully examined, it is seen that the foot raised up from the road surface is swung forwardly to shift the center of gravity, it falls in contact with the ground from the outside while the leg is in the state slightly inclined backwardly, the foot returns to the inside while the center of gravity is gradually shifted forwardly, and the heel separates from the ground and the foot makes an action of kicking the ground on the toe. In view of results of this examination, it has been decided that among various movements to be given to the footwear block, movements corresponding to the movements given by the leg should be given by the above-mentioned freely supporting mechanism and an inclining mechanism and movements corresponding to the movements given to the foot at the time of grounding should be given by another accompanying mechanism and by the vertical movement of the ground stand.

The present invention will now be described in detail by reference to an embodiment illustrated in the accompanying drawing, in which:

FIG. 2 is a partially disassembled perspective view showing the connection between the mechanism for supporting freely the footwear block and the mechanism for inclining the footwear block;

FIG. 5 is a disassembled perspective view of the pain parts of the tester illustrating the interconnection between the mechanism for supporting freely the footwear block and the mechanism for inclining the footwear block;

Figure 6:
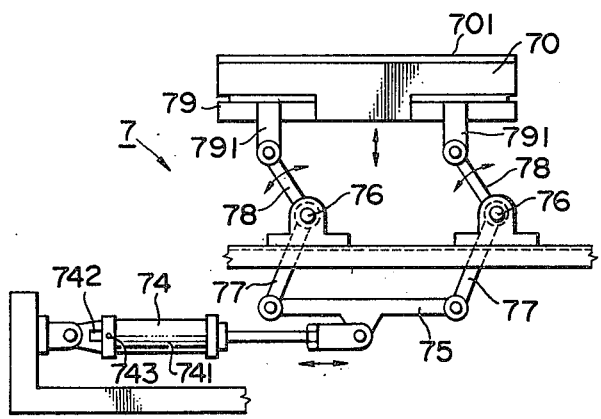

FIG. 6 is a side view of the mechanism for bringing up and down the ground stand; and FIGS. 7 to 11 are views illustrating principles of the movements at the respective parts, wherein FIGS. 7(A) and 7(B) are front and outer side views showing the state at the starting point, FIGS. 8(A) and 8(B) are front and outer side views showing the state midway of the retreating movement, FIGS. 9(A) and 9(B) are front and outer side views showing the state at the rear dead point, FIGS. 10(A) and 10(B) are front and outer side views showing the state midway of the advancing movement, and FIGS. 11(A) and 11(B) are front and outer side views showing the state at the front dead point.

The footwear tester constructed based on the above concept comprises a machine stand 1, a prime mover mechanism 2 mounted on the upper portion of the machine stand 1, a footwear block supporting mechanism 3 corresponding to the skeleton of the leg, which supports freely a footwear block 30 so that the footwear block 30 can automatically advance and retreat (in the present invention, "advancing" means shifting toward the toe and "retreating" means shifting toward the heel) and can bend in all the directions, a footwear block inclining mechanism 4 corresponding to the muscle of the leg, which performs changes of the posture of said mechanism 3 for supporting freely the footwear block 30, front operation mechanism 5 and rear operation mechanism 6 for controlling changes of the posture of said footwear block 30 from the outside, and a lift mechanism 7 for bringing up and down a ground stand 70, wherein said mechanism 3 for supporting freely the footwear block 30 and said footwear block inclining mechanism 4 are operated interconnectedly by the prime mover mechanism 2, said front operation mechanism 5 and rear operation mechanism 6 are operated in response to the operation of the mechanism 3 for supporting freely the footwear block 30, the operation of the lift mechanism 7 is indirectly controlled by the operation of an air cylinder in which introduction and discharge of fluid is electromagnetically controlled by the mechanism 3 for supporting freely the footwear block 30, and wherein said respective mechanisms are interconnected with one another so as to control changes of the posture of the footwear block 30.

Incidentally, in the present invention, the "front" and "rear" parts and "inside" and "outside" are defined based on the footwear block 30, so that the front part means the toe side and the rear part means the heel side and that the inside means the hallux side and the outside means the fifth finger side.

Figure 1:
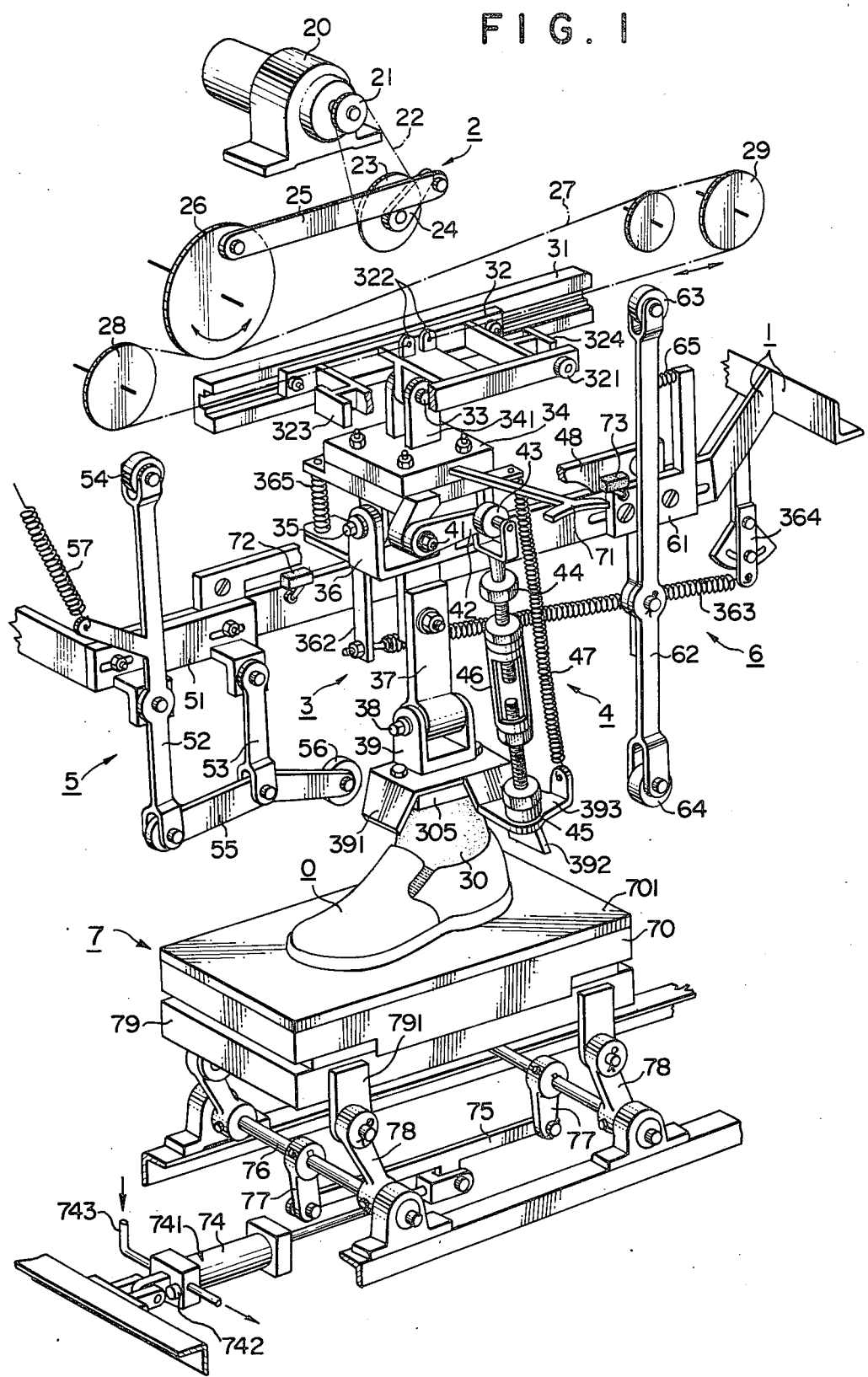
FIG. 1 is a partially cut-out perspective view showing the entire arrangement of the footwear tester according to the present invention.

The embodiment illustrated in the drawing will now be described. In this embodiment, all the mechanisms exclusive of the prime mover mechanism 2 are contained in the interior of the machine stand 1, and the tester is designed so that a footwear of one foot (the left foot in the drawing) is tested. FIG. 1 is a perspective view illustrating the entire arrangement. Referring to this FIG. 1, the prime mover mechanism 2 is mounted on the upper portion of the machine stand 1, and the mechanism 3 for supporting freely the footwear block 30 and the footwear inclining mechanism 4 are suspended from the ceiling of the machine stand 1. The front operation mechanism 5 and rear operation mechanism 6 are disposed in the front and rear portions of the machine stand 1 and the lift mechanism 7 is disposed in the lower portion of the machine stand 1.

The prime mover mechanism 2 comprises a non-staged variable speed electric motor 20, a sprocket 21, a chain 22, a sprocket 23, a crank arm 24, a crank lever 25, a sprocket 26, a chain 27 and sprockets 28 and 29. The rotation of the non-staged variable speed electric motor 20 is converted to reciprocative movements in the forward and backward directions of the chain laid out between the sprockets 28 and 29 through the movement transmission mechanism including the sprocket 21, chain 22, sprocket 23, crank arm 24, crank lever 25 and sprocket 26. In this prime mover mechanism 2, simple reciprocative movements may be generated by utilizing an electromagnetically controlled air cylinder or other fluid control mechanism instead of the above-mentioned transmission mechanism.

Figure 3:
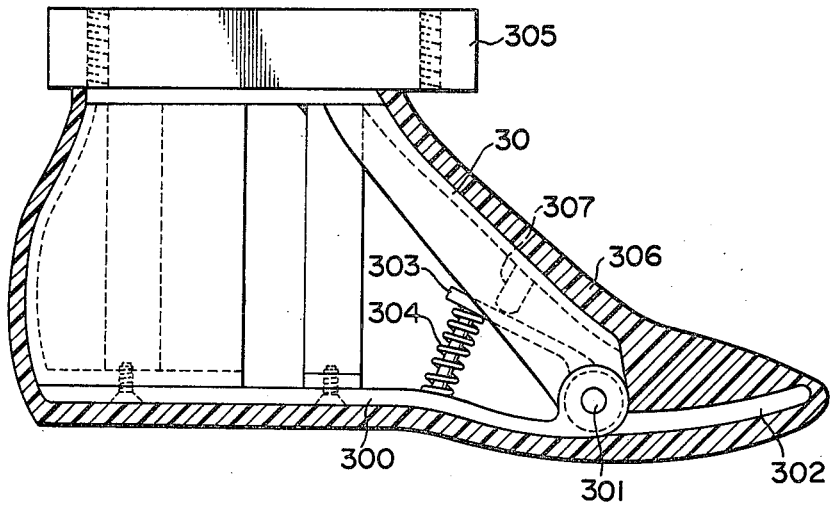
FIG. 3 is a partially cut-out side view of the footwear block.
Figure 4:
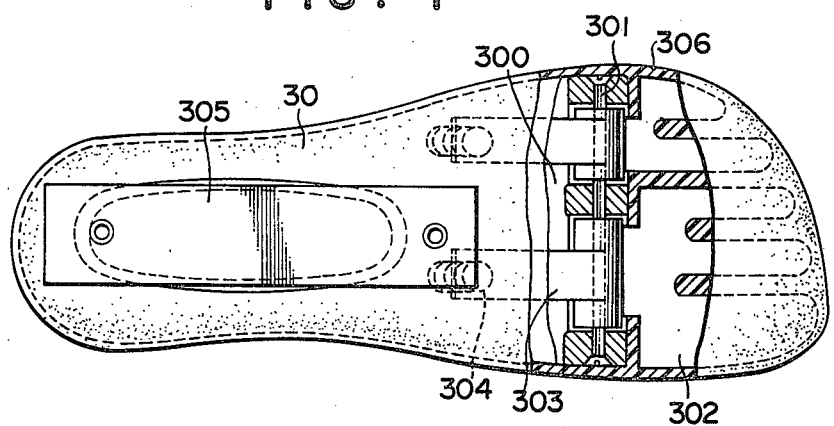
FIG. 4 is a partially cut-out plan view of the footwear block.

The mechanism 3 for supporting freely the footwear block comprises a footwear block 30, guide stand pieces 31 laid out in parallel to each other in the longitudinal direction in the ceiling portion of the machine stand 1, a mounting stand 32 slidably supported between said guide stand pieces 31, said mounting stand 32 including, as shown in FIG. 2, four wheels 321 disposed on the inner and outer sides, two chain stop pieces 322 projected in the upper portion and pressing pieces 323 and 324 disposed in the front and rear portions, a base plate 34 pivoted at a part 33 on the mounting stand 32 by means of an upper projection 341 so that it can turn in the longitudinal direction, a universal piece 36 including a stop piece 361, said universal piece being pivoted at a part 35 on a lower projection 342 of said base plate 34 so that it can turn in the lateral direction, a main arm 37 adjustably connected to the universal piece 36, and a footwear attachment stand 39 including pressing pieces 391 and 392 and projecting piece 393 projected in the longitudinal and lateral directions, respectively, said footwear attachment stand 39 being pivoted at a part 38 on the lower end of the main arm 37 so that it can turn in the lateral direction. The footwear block 30 is attached to the lower face of the footwear block attachment stand 39, and both the ends of the chain 27 are fixed to the upper two chain stop pieces 322, respectively, to connect the footwear block supporting mechanism 3 to the prime mover mechanism 2. The reason why the main arm 37 is adjustably connected to the universal piece 36 is that the contact angle between the ground stand 70 and the footwear block 30 which is attached to the main arm 37 through the footwear block attachment stand 39 can be adjusted. The stop piece 361 acts as a safety device for stopping rotation of the universal piece 36 by contact of the upper end of the stop piece 361 with the lower projection 342 when the universal piece 36 turns to the left. The above-mentioned structure of the footwear block supporting mechanism 3 is similar to the structure of the leg to the foot; namely, the pivoting part 33 inclining in the longitudinal direction and the pivoting parts 35 and 38 inclining in the lateral direction act as joints. A pulling spring 363 is inserted between the stop piece 362 connected to the universal piece 36 and the rear part of the machine stand 1 through a spring adjusting plate 364 and a compression spring 365 is inserted between the projection 343 of the base plate 34 and the universal piece 36, whereby the movements of the respective parts can be smoothened and the footwear block 30 can be elastically contacted with the ground. As shown in FIGS. 3 and 4, in the footwear block 30, a rotation shaft 301 is disposed in the front portion of the block body 300 at a part corresponding to the position of joints on the base of the phalange, and a toe portion 302 is connected to the rotation shaft 301. Springs 304 are interposed between a pressing piece 303 fixed to or integrated with the two portion 302 and the bottom face of the block body 300 so that the toe portion 302 can be turned elastically. The footwear block 30 further comprises a portion 305 (screw in this embodiment) for attachment of the footwear block 30 to the attachment stand 39, and the entire surface of the block body 300 is covered with a coating 306 composed of a rubber or elastic synthetic resin so that feeling resembling that of the muscle and skin is given to the footwear block 30. In the drawing, reference numeral 307 represents a stopper. The embodiment shown in the drawing may be modified so that a heating mechanism such as electric heating means is included in the interior of the block body 300 and toe portion 302 and a water-introducing and evaporating member is attached thereto to disperse steam heated to the body temperature to the outside through the water-permeable coating 306, whereby conditions resembling actual conditions of the foot can be produced.

The footwear block inclining mechanism 4 is attached to the footwear block supporting mechanism 3. As shown in FIGS. 1, 2 and 5, the footwear block inclining mechanism 4 comprises a rotation shaft 41 projected from the outer side face of the base plate 34, a guide arm 42 rotatably pivoted on the rotation shaft 41, a guide wheel 43 fixed to the guide arm 42, an adjustment rod 46 connecting the guide arm 42 to the projecting piece 393 through universal joints 44 and 45, a pulling spring 47 laid out between the projecting piece 344 on the outer side of the base plate 34 and the projecting piece 393, and a guide rail 48 laid out between the front and rear portions of the machine stand 1 in parallel to the guide stand 31, the lower face of the guide rail 48 pressing the guide wheel 43 being concaved and arcuated at the rear end thereof. Also a guide piece 71 for controlling the lift mechanism 7 described hereinafter is attached to the above-mentioned base plate 34.

As shown in FIG. 1, the front operation mechanism 5 comprises an attachment plate 51 disposed on the machine stand 1 so that its position can be freely adjusted, rotary arms 52 and 53 pivoted on the attachment plate 51, a guide wheel 54 attached to the upper end (corresponding to the height of the mounting stand 32) of one rotary arm 52, a front rod 55 to which the lower ends of both the rotary arm 52 and 53 are rotatably connected, a guide wheel 56 attached to the top end of the front rod 55 and a pulling spring 57 disposed between the rotary arm 52 and the machine stand 1 to return the rotary arm 52 to the regular position. The guide wheel 56 is located at a height falling in contact with the pressing piece 391.

Also as shown in FIG. 1, the rear operation mechanism 6 comprises an attachment plate 61 disposed on the machine stand 1 so that its position can be freely adjusted, a rotary arm 62 pivoted on the attachment plate 61, guide wheels 63 and 64 attached to the upper and lower ends of the rotary arm 62, respectively, and a compression spring 65 laid out between the rotary arm 62 and the attachment plate 61 to return the rotary arm 62 to the regular position. The guide wheel 63 is located at a height corresponding to that of the mounting stand 32 and the guide wheel 64 is located at a height corresponding to that of the pressing piece 392.

As shown in FIGS. 1 and 6, the lift mechanism 7 comprises a guide piece 71 attached to the above-mentioned base plate 34, front and rear limit switches 72 and 73 to be put on and off by passage of the guide piece 71, an air cylinder 74 electromagnetically valve-controlled and operated by both the limit switches 72 and 73, said air cylinder including therein a spring having one end pivoted on the machine stand 1, a rod 75 pivoted on the cylinder head of the air cylinder 74, rotation shafts 76 mounted on the machine stand 1 to extend in the lateral direction, arms 77 having one ends fixed to the rotation shafts 76 and the other ends pivoted on both the ends of the rod 75, four arm pieces 78 of the same size and configuration having the lower ends fixed to the rotation shafts 76 and being arranged in a square form, a base stand 79 having legs 791 fixed to the lower face thereof at four corners, said fixed legs 791 being pivoted on said four arms 78, respectively, and a ground stand 70 dismountably fitted on the upper face of the base stand 79. A number of ground stands 70 are prepared, and surface plates 701 differing in the surface conditions corresponding the road surface conditions are disposed on the ground stands 70, respectively, so that the test can be conducted under various conditions. The lift mechanism 7 is designed so that the surface of the ground stand 70 is raised to a point slightly higher than the bottom face of the footwear block 30.

Of course, various accessory members and means, such as switches, meters and protecting plates, may be attached to the tester having the above-mentioned structure, and in general, two testers for the right foot and for the left foot are disposed in one machine stand 1 and they are operated by one prime mover mechanism 2. In this case, the two testers for the right foot and for the left foot are disposed symmetrically with respect to the longitudinal axis. As pointed out hereinabove, the term "outside" means the left side in the tester for the left foot. Accordingly, in the tester for the right foot, the term "outside" means the right side.

The operation of the footwear tester of the present invention having the above-mentioned structure will now be described A valve (not shown) of an air feed pipe 743 connected to the air cylinder 74 is opened and the ground stand 70 is manually brought down. A footwear O (a high shoe is illustrated in the simplified manner in FIGS. 7 to 11) is fitted on the footwear block 30, and it is attached to the lower face of the footwear block attachment stand 39. The ground stand 70 having a surface plate 701 having surface conditions corresponding to the intended road surface conditions is fitted on the base stand 79. Then, the valve of the air feed pipe 743 is closed and the non-staged variable speed motor 20 is actuated to initiate the operation. When the prime mover mechanism 2 is actuated, by the chain 27 connected to the prime mover mechanism 2 the mounting stand 32 is reciprocated in the longitudinal direction at a predetermined frequency between the front dead point and rear dead point. When the mounting stand 32 retreats from the starting point shown in FIG. 7, the guide piece 71 first passes through the rear limit switch 73 and air is supplied to the air cylinder 74 to suck the cylinder head, and simultaneously, the base stand 79 is lifted up to initiate the rising of the surface plate 701 of the ground stand 70. Accordingly, the surface plate 701 is caused to come in contact with the sole face of the footwear O fitted on the footwear block 30 and it is moved slightly backwardly in this state (see FIG. 8). When the guide wheel 43, which is usually pressed to the lower edge of the guide rail 48 by the pulling spring 47, arrives at the arcuated portion in the rear part of the guide rail 48, the adjustment rod 46 is brought down to press the projecting piece 393 and to throw down the footwear block 30 outwardly with the pivoting parts 35 and 38 being as the center. As a result, the outside portion of the sole of the footwear O is caused to come in contact with the surface plate 701 (this operation will hereinafter be referred to simply as "grounding"). When the mounting stand 32 is further retreated, the pressing piece 324 of the mounting stand 32 comes in contact with the guide wheel 63 of the rear operation mechanism 6 and the rotary arm 62 is turned and the guide wheel 64 is pressed to the pressing piece 392, whereby the retreating movement of the footwear block 30 is hindered, and the footwear block supporting mechanism 3 including the main arm 37 is backwardly inclined and also the footwear block 30 is backwardly inclined (see FIG. 9). At this point, the sole face of the footwear O is contacted with the surface plate 701 in the heel portion. Further, at this point, since the pressure on the guide wheel 64 is highest when the mounting stand 32 arrives at the rear dead point (turning point) and since the sole face of the footwear O confronts the surface plate 701 at a maximum angle and the contact area is small, there is a risk that the footwear block 30 will be pressed out forwardly. In this embodiment, this risk is eliminated by diminishing the force of pressing out the footwear block 30 by means of the spring 363. When the mounting stand 32 changes its moving direction at the rear dead point (turning point) and begins the advancing movement, the main arm 37 and all the members having contact therewith begin to incline forwardly, and when the guide wheel 43 passes through the arcuated portion of the guide rail 48, the lateral inclination is removed the original state is restored, and simultaneously, the footwear block 30 is brought down by the action of the adjustment rod 46 to ground the entire sole face of the footwear O and the ground stand 70 is brought down against the pressure of the air cylinder 74. The operation during the above-mentioned state is one reproducing the trampling operation where the body weight is imposed during walking (see FIG. 10).

The mounting stand 32 advances while leaving the footwear block 30 pressed to the central portion of the surface plate 701 by friction, and the footwear block supporting mechanism 3 including the main arm 37 is inclined forwardly. When the guide wheel 54 is thus caused to come in contact with the pressing piece 323 of the mounting stand 32, the rotary arms 52 and 53 are operated in the interconnected state to cause the guide wheel 56 on the top end of the front rod 55 to press the pressing piece 391, whereby the forward inclination of the footwear block 30 is enhanced. Substantially at the same time, the guide piece 71 passes through the limit switch 72 to feed air to the air cylinder 74, and the cylinder head is pushed out to push down forwardly the rod 75 and the base stand 79 and ground stand 70 cooperating therewith. Finally, a sliding movement is caused and the toe portion separates from the ground stand 70. In this case, the tow portion 302 of the footwear block 30 is bent against the force of the spring 304 and the kick-up operation during walking is reproduced (see FIG. 11). When the mounting stand 32 turns at the front dead point (turning point) and then retreats, since the ground stand 70 is brought down though not shown specifically in the drawing, the footwear block supporting mechanisms 3 having the footwear block 30 attached thereto can be returned to the starting point without any resistance, and the foregoing procedures are conducted repeatedly. Thus, the walking operation can be faithfully reproduced according to the present invention.

In the footwear tester of the present invention, the angle of connecting the main arm 37 to the universal piece 36 and the position of the adjustment rod 46 are adjusted according to the kinds of the footwear block 30 and the footwear O attached thereto so that the angle of grounding the footwear block 30 to the ground stand 70 can be appropriately adjusted. Further, the attachment positions of the attachment plate 51 and the attachment plate 61 are adjusted so as to adjust the time for initiation of inclination in the footwear block 30. Still further, the elasticity of the spring 363 is adjusted by the spring adjusting plate 364 so that a force sufficient to prevent sliding on grounding is given. Still in addition, the pressure of grounding of the footwear block 30 on the ground stand 70 can be controlled by adjusting the pressure of air fed to the air cylinder 74. Thus, various adjustments can be performed by means various accompanying mechanisms and therefore, the durability test can be accomplished under various conditions and results comparable to results of the practical wearing test can be effectively obtained.

As will be apparent from the foregoing illustration, according to the footwear tester of the present invention, grounding of the heel in the laterally inclined state at the time of trampling, shifting of the center of gravity in the grounded state at the time of treading, shifting of the center of gravity in the laterially non-inclined state at the time of kicking and deformations of the foot during walking can be reproduced very faithfully. Namely, various walking conditions can be faithfully reproduced and the durability test can be accomplished without any limitation of the time. Moreover, data from which influences by changes of the road surface conditions can be anticipated can readily be obtained. Because of these epoch-making properties of the tester of the present invention, the durability test conducted by using the tester of the present invention can satisfactorily replace the practical wearing test. Still further, the tester of the present invention is advantageous in that data under specific road condtions can readily be obtained.

What is claimed is:

1. A tester of footwear comprising a machine stand, a prime mover mechanism mounted on the upper portion of the machine stand to give reciprocative movements repeatedly in the longitudinal direction of said footwear, a supporting mechanism for supporting freely a footwear block for attachment of said footwear so that the footwear block can be advanced and retreated and can be bent in all directions, a footwear block inclining mechanism attached to the footwear block supporting mechanism to slightly incline the footwear block in the lateral direction of said footwear only when the footwear block supporting mechanism is retreated, a front operation mechanism disposed in the machine stand to incline forwardly the posture of the footwear block when the footwear block supporting mechanism is located in the vicinity of the front dead point, a rear operation mechanism disposed in the machine stand to incline backwardly the posture of the footwear block when the footwear block supporting mechanism is located in the vicinity of the rear dead point and a lift mechanism for bringing up and down a ground stand so that the ground stand is in the brought-down state during a period from the point when the footwear block supporting mechanism is advanced to the front dead point to the point when the footwear block supporting mechanism is retreated to a point intermediate the front dead point and the rear dead point, wherin when the tester is driven, the respective mechanisms are interconnected with each other so that longitudinal inclination, lateral inclination, grounding operation and kick-up operation resembling those imparted to the foot during practical walking are given to the footwear block.

2. A tester as set forth in claim 1 wherein the prime mover mechanism comprises an electric motor and a movement transmission mechanism for converting mechanically the rotating movement of the electric motor to a reciprocative movement in the longitudinal direction.

3. A tester as set forth in claim 1 wherein the footwear block supporting mechanism comprises a footwear block, a mounting stand having a reciprocative movement in the longitudinal direction in the upper portion of the machine stand, a base plate connected to and suspended from the mounting stand through several stages of joints so that it can bend in all directions a universal piece, a main arm and a footwear block attachment stand connected to said main arm.

4. A tester as set forth claim 3 wherein the footwear block inclining mechanism comprises an adjustment rod having a guide wheel on the top end thereof, which is bendably inserted between the outer side face of the base plate and the outer side face of the footwear block attachment stand, a guide rail 48 laid out in the longitudinal direction of the machine stand, and a pulling spring disposed to press the guide wheel to the guide rail.

5. A tester as set forth in claim 3 wherein the front operation mechanism comprises an attachment plate, rotary arms and pivoted on the attachment plate to constitute a parallel crank mechanism, a front rod, a guide wheel mounted on the top end of the rotary arm and a guide wheel mounted on the top end of the front rod, the guide wheel being located at the same height as that of the mounting stand and the guide wheel being located to confront a pressing piece disposed in the front of the footwear block attachment stand.

6. A tester as set forth in claim 3 wherein the rear operation mechanism comprises an attachment plate, a rotary arm pivoted on the attachment plate, guide wheels and attached to the upper and lower ends of the rotary arms, respectively, and a compression spring for returning the rotary arm to the regular position, the guide wheel being located at the same height as that of the mounting stand and the guide wheel being located to confront a pressing piece disposed in the rear of the footwear block attachment stand.

7. A tester as set forth in claim 3 wherein the lift mechanism comprises a guide piece attached to the base plate, front and rear limit switches which are put on and put off by said guide piece, an air cylinder operated by said two limit switches, a base stand driven and brought up and down by said air cylinder through a double parallel link mechanism, and the ground stand being dismountably fitted on the base stand.

8. A tester as set forth in claim 1 wherein the footwear block comprises a footwear block body, a rotation shaft disposed in the front portion of said body at a part corresponding to the position of joints on the base of the phalange and a pressing piece fixed to the toe portion of said body, a spring being contacted with said pressing piece so that an operation resembling the bending operation of the fingers can be attained.

9. A tester as set forth claim 1 wherin the outer surface of the footwear block is coated with a covering composed of a rubber or elastic synthetic resin.

10. A tester as set forth in claim 1 wherein a surface plate having surface conditions corresponding to specific road conditions is laid out on the surface of the ground stand.

* * * * *